(12) United States Patent
Asada et al.

(10) Patent No.: US 10,867,377 B2
(45) Date of Patent: Dec. 15, 2020

(54) DETERMINING SOIL STATE AND CONTROLLING EQUIPMENT BASED ON CAPTURED IMAGES

(71) Applicant: Massachusetts Institute of Technology, Cambridge, MA (US)

(72) Inventors: Haruhiko Harry Asada, Lincoln, MA (US); Filippos Edward Sotiropoulos, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 6 days.

(21) Appl. No.: 15/851,526

(22) Filed: Dec. 21, 2017

(65) Prior Publication Data

US 2018/0174291 A1    Jun. 21, 2018

Related U.S. Application Data

(60) Provisional application No. 62/437,428, filed on Dec. 21, 2016.

(51) Int. Cl.
| | |
|---|---|
| *G06T 7/00* | (2017.01) |
| *E02F 9/20* | (2006.01) |
| *G01N 33/24* | (2006.01) |
| *G06T 7/246* | (2017.01) |
| *E02F 9/26* | (2006.01) |

(52) U.S. Cl.
CPC .......... *G06T 7/0002* (2013.01); *E02F 9/2025* (2013.01); *G01N 33/24* (2013.01); *G06T 7/0004* (2013.01); *G06T 7/246* (2017.01); *G06T 7/97* (2017.01); *E02F 9/261* (2013.01); *G06T 2207/30181* (2013.01)

(58) Field of Classification Search
CPC ......... G06T 7/0002; G06T 7/246; G06T 7/97; G06T 2207/30181; E02F 9/2025; E02F 9/261; G01N 33/24
See application file for complete search history.

(56) References Cited

U.S. PATENT DOCUMENTS 5,462,122 A * 10/1995 Yamamoto .............. E02F 3/842
                                                                 172/2
6,085,583 A    7/2000 Cannon et al.
(Continued)

FOREIGN PATENT DOCUMENTS

CN          102565058 A       7/2012
DE    10 2012 112 740 A1      6/2014
(Continued)

OTHER PUBLICATIONS

Google Scholar Search Results.*
(Continued)

*Primary Examiner* — Qun Shen
(74) *Attorney, Agent, or Firm* — Wolf, Greenfield & Sacks, P.C.

(57) ABSTRACT

Methods and systems for controlling earth moving equipment are described. In some embodiments, a stream of images may be captured using at least one imaging system. At least one state of soil may be determined in real time relative to the earth moving equipment based on the captured stream of images. At least one aspect of the earth moving equipment's operation may then be controlled based on the determined at least one state of the soil.

23 Claims, 10 Drawing Sheets

(56) References Cited

U.S. PATENT DOCUMENTS

| | | | |
|---|---|---|---|
| 6,223,110 | B1 | 4/2001 | Rowe et al. |
| 6,363,632 | B1 | 4/2002 | Stentz et al. |
| 6,736,216 | B2 | 5/2004 | Savard et al. |
| 7,669,354 | B2 | 3/2010 | Aebischer et al. |
| 8,838,331 | B2 | 9/2014 | Jensen |
| 8,930,091 | B2 | 1/2015 | Uperoft et al. |
| 9,014,924 | B2 | 4/2015 | Edara et al. |
| 2007/0144042 | A1* | 6/2007 | Miskin .............. E02F 3/6481 37/381 |
| 2012/0098933 | A1* | 4/2012 | Robinson ............. G06T 7/579 348/46 |
| 2012/0114181 | A1 | 5/2012 | Borthwick et al. |
| 2014/0177932 | A1* | 6/2014 | Milne .............. G01N 15/1475 382/128 |
| 2014/0300732 | A1* | 10/2014 | Friend ................. G06T 7/73 348/135 |
| 2016/0029547 | A1* | 2/2016 | Casper ............... A01B 63/002 701/50 |
| 2016/0094806 | A1 | 3/2016 | Hasejima et al. |
| 2016/0170090 | A1* | 6/2016 | Collins ............... G01V 99/00 702/5 |
| 2016/0219215 | A1* | 7/2016 | Sasaki ................ G01C 11/06 |
| 2016/0230369 | A1* | 8/2016 | Kaneko ............... B60W 20/00 |
| 2016/0258128 | A1 | 9/2016 | Nakamura et al. |
| 2016/0275218 | A1* | 9/2016 | Shuler ............... G06F 17/5009 |
| 2017/0049053 | A1* | 2/2017 | Bonefas .............. G06T 7/70 |

FOREIGN PATENT DOCUMENTS

| | | |
|---|---|---|
| WO | WO 2005/103396 A | 11/2005 |
| WO | WO 2016/159839 A | 10/2016 |

OTHER PUBLICATIONS

[No Author Listed], Motion Metrics Product Brochure, Motion Metrics International Corp., Vancouver, B.C., Canada. 2015, 10 page brochure. 6 page pdf.

Argyriou, Sub-hexagonal phase correlation for motion estimation. IEEE Trans on Image Processing, Jan. 2011;20(1):110-20. Epub Jul. 12, 2010.

Buscombe, Transferable wavelet method for grain-size distribution from images of sediment surfaces and thin sections, and other natural granular patterns. Sedimentology. Dec. 2013;60(7):1709-32. Epub Jun. 6, 2013.

Farneback, Two-frame motion estimation based on polynomial expansion. In: Image Analysis. SCIA '03, Proc of the 13th Scandinavian Conf on Image Analysis. Lecture Notes in Computer Science, vol. 2749. 2003. Halmstad, Sweden: Springer-Verlag. pp. 363-370.

Gonzalez et al., Digital Image Processing, Second Edition. Ch. 9, pp. 528-535. Prentiss Hall, Upper Saddle River, NJ. 2002.

Horn et al., Determining optimal flow. Artificial Intelligence. 1981;17:185-203.

Lucas et al., An iterative image registration technique with an application to stereo vision. In: IJCAI 1981: Proc of the $7^{th}$ Intl Joint Conf on Artificial Intelligence, Aug. 24-28, Vancouver, British Columbia, vol. 2, pp. 674-679. 1981, Morgan Kaufmann Publishers, Inc., San Francisco, CA, USA. Essentially same as Proceedings DARPA Image Understanding Workshop, Apr. 1981, pp. 121-130.

McKyes et al., The cutting of soil by narrow blades. J Terramechanics. Jun. 1977;14(2):43-58.

Xu et al., Survey of clustering algorithms. IEEE Trans on Neural Networks. May 2005;16(3):645-78.

International Search Report and Written Opinion dated Feb. 26, 2018 for Application No. PCT/US2017/067910.

\* cited by examiner

US 10,867,377 B2

DETERMINING SOIL STATE AND CONTROLLING EQUIPMENT BASED ON CAPTURED IMAGES

CROSS-REFERENCE TO RELATED APPLICATION

This application claims the benefit of priority under 35 U.S.C. § 119(e) to U.S. Provisional Patent Application No. 62/437,428 filed on Dec. 21, 2016, the contents of which are incorporated herein by reference in their entirety.

BACKGROUND

Systems for autonomous excavation are being developed. However, autonomous excavation systems are not widely in use and suffer from various limitations as detailed further herein.

SUMMARY

Some aspects include a device for controlling earth moving equipment, the device comprising: at least one processor configured to determine at least one state of soil in real time relative to the earth moving equipment based on a captured stream of images; and control at least one aspect of the earth moving equipment's operation based on the determined at least one state of the soil.

Additional aspects include a method for controlling earth moving equipment, the method comprising: determining at least one state of soil in real time relative to the earth moving equipment based on a captured stream of images; and controlling at least one aspect of the earth moving equipment's operation based on the determined at least one state of the soil.

Further aspects include at least one computer-readable medium having instructions thereon that, when executed by at least one processor, perform a method for controlling earth moving equipment, the method comprising: determining at least one state of soil in real time relative to the earth moving equipment based on the captured stream of images; and controlling at least one aspect of the earth moving equipment's operation based on the determined at least one state of the soil.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings.

DETAILED DESCRIPTION

Figure 1:
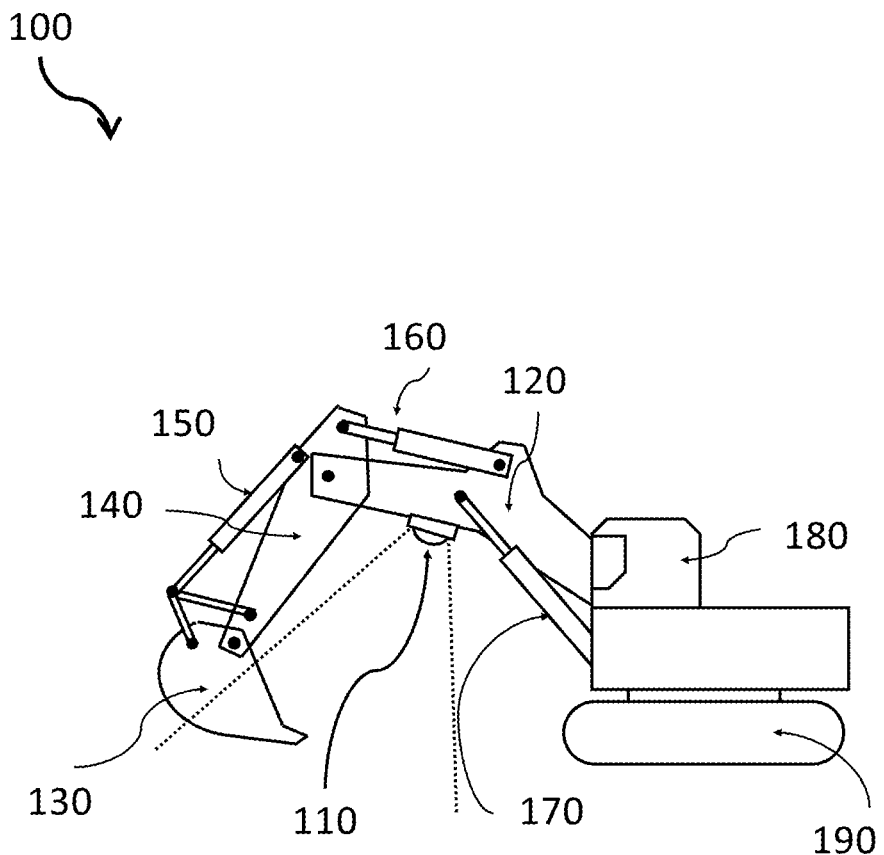
FIG. 1 is a side view of exemplary earth moving equipment, in accordance with some embodiments.

The inventors have recognized and appreciated that conventional excavation systems typically require a human operator to look at the bucket of the earth moving equipment to accurately and efficiently determine the fill rate of the bucket. A human operator uses this determination to control the equipment. However, to date, automated control systems have found it difficult to accurately determine the operating state of excavating equipment and filling rates of buckets to control these systems.

In view of the above, the inventors have recognized and appreciated that controlling earth moving equipment while an excavation is in progress may be possible by determining one or more soil states of soil adjacent to and/or within the container or bucket of an excavation system. Specifically, inventors recognized and appreciated that the state of disturbed soil may be quantified throughout an excavation cycle via image processing of an image stream from one or more imaging systems. Processing of this image stream may be used to estimate the flow rate of soil into and/or around a bucket. The inventors have recognized and appreciated that this quantification may also be used to determine a fill rate and/or level of the bucket, as well as to determine other properties of the soil, such as soil movement, soil profile, obstacle location, shear boundary location, soil friction angle, and soil granularity. These determined one or more soil states may then be used to control one or more aspects of the operation of an excavation system.

In the above noted embodiment, the inventors have recognized and appreciated that certain image processing techniques can be used to determine various information related to the state of the soil, including flow rates such as the flow rate into the container, around the container, in a lateral direction (or any other direction) relative to the container, and/or out of the container, as well as soil properties such as a shear failure surface of the soil, a friction angle of the soil, and a granularity of the soil.

Soil state as well as movement into and/or near a bucket may be determined in any number of ways. For example, image processing may detect changes in the absolute magnitude, rate of change, and/or the direction of a flow of soil relative to a bucket to determine one or more soil states for a system. Furthermore, image processing may track the flow of soil through a predetermined region into a bucket, lateral movement of soil relative to a digging direction of a container (e.g. lateral movement of soil away from or towards the side edges of a bucket), as well as movement away from the bucket such as soil moving away from a leading edge of the bucket. Changes in soil flow velocity magnitude; direction of soil flow; soil flow velocity being greater than or less than a magnitude threshold; inflection points; and/or rates of change of these parameters may be used to identify particular soil states for use in controlling operation of an excavation system as detailed further below.

The inventors have recognized and appreciated that particular soil states, such as a fill level of a container, may be determined using thresholds, morphological transformations, and/or the detection of inflection points for the flow of soil within and/or surrounding a container during a digging cycle. For example, an inflection point in the filling rate and/or a velocity of a flow of soil into and/or away from a bucket may correspond to a point where soil either slows down and/or stops flowing into the bucket such that the flow of soil either stalls or is pushed outwards relative to the bucket. Alternatively, the flow rate and/or soil flow velocity falling below a preset threshold may correspond to a filled bucket condition. In either case, at this point, it may be difficult, or even counterproductive to try to add soil to the bucket.

The above noted methods of determining soil state may be used to control a number of operations of a piece of earth moving equipment. For example, the inventors have recognized and appreciated that accurately determining bucket fill level may improve the efficiency of operation of the equipment and prevent unnecessary wear. In one such embodiment, the one or more determined soil states noted above may be used by a system to control operation of a digging cycle. In one such embodiment, the determined soil state may be used to control one or more of a trajectory of a container during a digging portion of a digging cycle and/or to end a digging cycle by scooping a container. Such an operation may be optimized to end digging operations at an accurately identified optimal fill level of a bucket as contrasted to continuing to dig after the bucket is filled which may lead to accelerated wear and damage to the system.

In one embodiment, the inventors have recognized and appreciated that effective techniques for controlling earth moving equipment may include capturing a stream of images from at least one imaging system, determining at least one state of soil in real time relative to the earth moving equipment based on the captured stream of images, and controlling at least one aspect of the earth moving equipment's operation based on the determined at least one state of the soil. Such techniques may also include determining the at least one state of the soil at least by determining a total amount of soil in at least one container of the earth moving equipment based on at least one flow rate.

In another embodiment, the inventors have recognized and appreciated that effective techniques for controlling earth moving equipment may also include detecting areas of soil movement within a field of view, and determining at least one state of the soil based on the identified areas of soil movement within the field of view. Such techniques may also include identifying areas of soil movement in areas surrounding the container such as in front of a leading edge, adjacent the opposing sides of the container, and/or any other appropriate area adjacent the container of the earth moving equipment. At least one state of the soil may then be determined based on the identified areas of soil movement. For example, movement of soil in front of the leading edge of the at least one container of the earth moving equipment and/or soil movement laterally away from one or more sides of a bucket relative to a digging direction of the container may be used to determine one or more soil states. These determined one or more soil states, which may include a fill level of the container, may then be used to control operation of the excavation system.

In the above embodiment, soil movement may either be detected within a predetermined portion of a field of view (e.g. in front of a leading edge of a container) and/or portions of the field of view in which soil is moving may be identified in real time and subsequently monitored to determine the desired one or more soil states. Specific embodiments in which these separate methods are employed for evaluating movement of soil are described further in relation to the figures below.

The inventors have recognized and appreciated that effective techniques for controlling earth moving equipment may further include determining the at least one state of the soil at least by evaluating differential motion between two or more image frames of a captured stream of images. For example, identifying differential motion between two or more image frames may be used to identify movement of soil particles and/or other material entrained in the soil that may be used to help determine one or more soil states and/or movement of the soil surrounding and/or within a corresponding bucket of the excavation system.

In some embodiments, and as elaborated on further below, the inventors have also recognized and appreciated that a soil state may include at least one flow rate of the soil in one or more directions relative to at least one container of an earth moving equipment. Additionally, the inventors have recognized and appreciated that the at least one state of the soil may comprise at least one property of the soil as detailed previously.

The terms bucket and container are both used in the current disclosure in various exemplary embodiments. However, it should be understood that these terms may be used interchangeably and that they both refer to a container of a piece of earth moving equipment that is constructed and arranged to dig and/or hold soil or other materials within the container during an excavation process. Therefore these terms may be used interchangeably and are not intended to be exclusive of one another.

For the sake of clarity, in some embodiments, an excavator or other specific piece of earth moving equipment is described. However, it should be understood that the various embodiments described herein are not limited to any particular type of earth moving equipment. Accordingly, any embodiments in which a particular piece of earth moving equipment is described may be considered as being applicable to other generic types of earth moving equipment as well as the current disclosure is not limited in this fashion.

Turning now to the figures, exemplary embodiments of implementations are discussed below. However, it should be appreciated that the disclosed embodiments are not limited to operating in accordance with any of these illustrative embodiments, as other embodiments are possible. Additionally, the various components, systems, and methods may be used either individually and/or in any appropriate combination as the disclosure is not so limited.

FIG. 1 is a side view of exemplary earth moving equipment 100, in accordance with some embodiments. It should be understood that while a particular embodiment of a piece of earth moving equipment has been depicted, the current disclosure is not so limited. For example, the earth moving equipment 100 may include a front shovel, excavator, loader, cable excavator, dragline excavator, and/or any other suitable equipment.

In the depicted embodiment, the earth moving equipment 100 includes stick 140, which may be rotatably attached between boom/arm 120 and container 130. Additionally, earth moving equipment 100 may include hydraulic cylinder 150, which may be rotatably attached between stick 140 and container 130. In some embodiments, earth moving equipment 100 may also include stick hydraulic cylinder 160, which may be rotatably attached between stick 140 and boom/arm 120. Additionally, earth moving equipment 100 may include boom hydraulic cylinder 170, which may be rotatably attached between boom/arm 120 and the chassis of the earth moving equipment 100. The various hydraulic cylinders may be used to control the orientation of the boom, stick, and container during operation.

In some embodiments, earth moving equipment 100 may also include an operator cab 180, which may provide housing for an operator, who may merely monitor earth moving equipment 100 or may control some operations. Additionally, earth moving equipment 100 may include tracks 190, wheels, legs, or any other suitable locomotion or positioning mechanism.

In some embodiments, earth moving equipment 100 may also include an imaging system 110. For example, imaging system 110 may include one or more detectors such as an RGB or monochrome camera, a 3D/depth camera, a structured light scanner, a time-of-flight camera, 3D LIDAR, and/or any other component capable of imaging a or otherwise detecting the presence and/or movement of material surrounding and/or within the container 130 (such as a bucket) of the earth moving equipment 100 as it is being operated to fill the container with soil or other material.

In some embodiments, at least one component of the imaging system 110 is positioned to have a view of the container 130 and at least a portion of the soil in the vicinity of the earth moving equipment 100 and/or specifically the container 130 during operating. For example, imaging system 110 may be positioned along a boom (or an arm) 120 of the earth moving equipment 100. However, regardless of where the one or more detectors are positioned, the one or more detectors are configured and arranged such that a field of view of the one or more detectors may either be aligned such that the container is positioned within a field of view and/or the one or more detectors and/or the one or more detectors may be capable of tracking the container to maintain it within a field of view of the one or more detectors during operation. Thus, in some embodiments, imaging system 110 may be rigidly connected to the earth moving equipment 100 or it may be connected with one or more degrees of freedom. For example, imaging system 110 may maintain its view of the container 130 and the soil based on the motion range of the boom/arm 120 with pre-mapped view angles and equipment angles. Alternatively, the imaging system 110 may track a feature on the container 130, boom/arm 120, or other appropriate component. In either case, the one or more detectors may provide a stream of images of the container and/or the surrounding soil to a corresponding controller, not depicted.

According to some embodiments, imaging system 110 may be positioned and designed to avoid damage to itself and the earth moving equipment 100 during operation. For example, the imaging system may be arranged so that it does not interfere with movement of the boom, stick, or other component of an associated piece of earth moving equipment during operation. Additionally, to reduce maintenance of the imaging system 110, the one or more detectors may have a special lens coating, such as hardened and/or anti-static coatings, that are configured to maintain lens cleanness and image clarity.

Figure 2A:
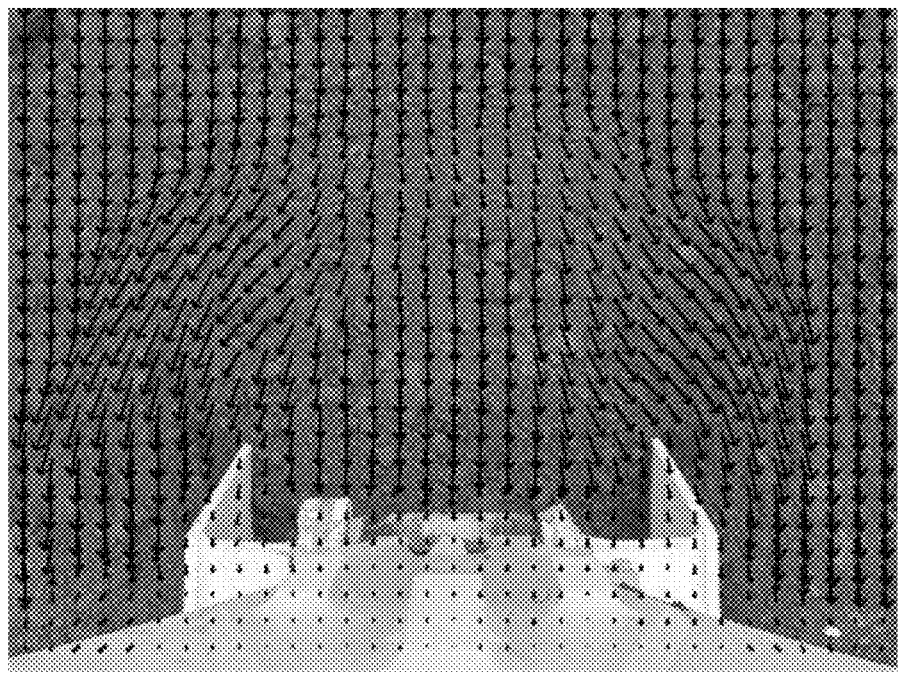
FIG. 2A is an exemplary image frame captured by an imaging system, in accordance with some embodiments.
Figure 2B:
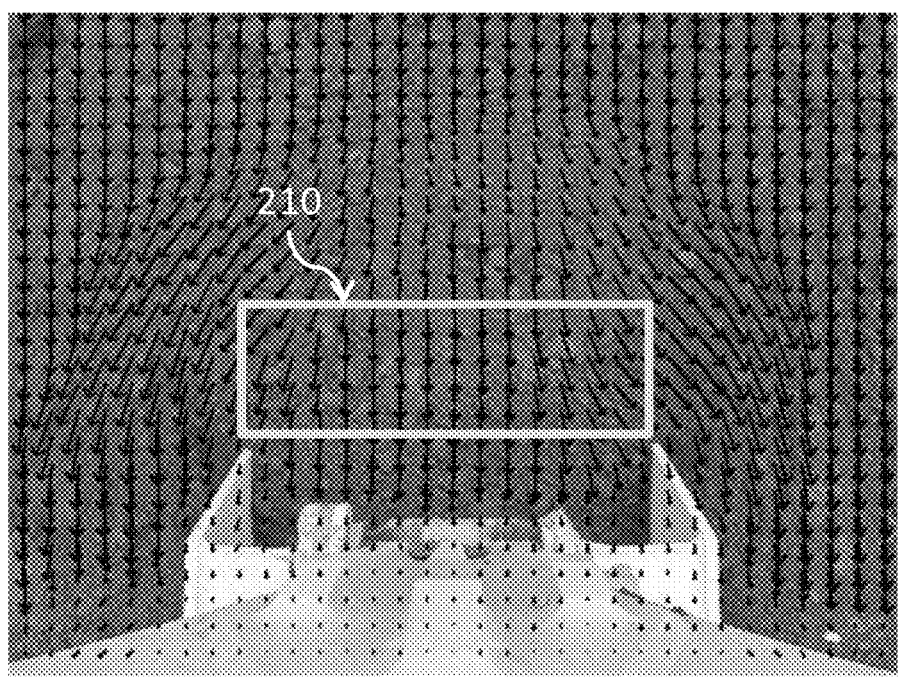
FIG. 2B is an exemplary image frame captured by an imaging system with a superimposed exemplary region, in accordance with some embodiments.

FIG. 2A is an exemplary image frame captured by an imaging system, in accordance with some embodiments. FIG. 2B is an exemplary image frame captured by an imaging system with an exemplary region 210 superimposed at a leading edge of the container of the system, in accordance with some embodiments. In some embodiments, an imaging system may capture a stream of images, which may have a similar field of view to FIGS. 2A and 2B. Operation of a piece of earth moving equipment relative to the flow of soil depicted in these figures is described in further detailed below.

According to some embodiments, a device (which may be connected to a piece of earth moving equipment an imaging system, or may be part of an imaging system) may process a captured stream of images to determine at least one soil state in real time relative to the a piece of earth moving equipment based on the captured stream of images. For example, the device may determine the state of the soil at least by evaluating differential motion between two or more image frames of the captured stream of images. In some embodiments, the device may identify areas of soil movement within the field of view of the imaging system, and determine the state of the soil based on the identified areas. For example, FIG. 2A depicts areas of soil movement relative to the container that may be used to determine one or more soil states. Alternatively or additionally, soil movement within a predetermined portion of a field of view may be used to determine the movement of soil into and/or away from the container. For example, in FIG. 2B, the predetermined portion of the field of view 210 is located in front of a leading edge of the container as the container is operated to scoop material into the container. Movement of soil through this predetermined portion of the field of view may then be used to estimate the amount of soil that has entered the container and/or whether the material is being pushed away indicating that the bucket is full as elaborated on further below. While movement of the soil relative to the front of the container is discuss above, movement of soil relative to the sides of the container may also be monitored as the disclosure is not so limited. Additionally, embodiments in which movement of the soil within the field of view is detected and then monitored over time to determine a soil state, as compared to looking at the movement of soil within the predetermined portion of the field of view in FIG. 2B, are also contemplated.

The inventors have recognized and appreciated that a number of methods (which may be referred to herein as optical flow) may be used to evaluate the differential motion soil, rocks, and/or other material surrounding and/or within a container between captured image frames. For example, these methods may include the Lucas-Kanade method, the Horn-Schunck method, the Farnebäck method, and phase correlation, as well as any other suitable differential motion evaluation method.

The inventors have recognized and appreciated that tracking soil movement between image frames may use most or all of the soil in the field of view, and so each pixel in the image frames may be used in the evaluation (with each pixel being a "feature"), such as in Farnebäck's method. Alternatively, a distinct set of features may be used in the evaluation, with each feature comprising a region of more than one pixel. In some embodiments, evaluating the differential motion may yield a flow quantity for each pixel of the image frames. The inventors have recognized and appreciated that this flow quantity may be equivalent to the velocity of each pixel. However, due to noise in the image frame sequence and image artefacts inherent in the video stream, there may often be spurious flow results at certain points. The inventors have recognized and appreciated that various methods may be used to alleviate this noise. For example, in some embodiments, a 2-dimensional median filter with a kernel size of 5 by 5, or any other appropriate sizing, may be used. If images are much noisier, the inventors have recognized and appreciated that an alternative method of flow adapted anisotropic diffusion may work well for analysis of the image stream.

The inventors have recognized and appreciated that in embodiments where one or more detectors of an imaging system are connected to a boom, arm, or other moving component of a system, it may be desirable to correct for movement of the portion of the system the detector is connected to. For example, movement of the image may be corrected to provide movement of the soil or other material within a field of view relative to a global reference frame. The inventors have recognized and appreciated that this correction may be made by taking a portion of an image, such as a strip of the image, sufficiently removed from a region of failure and/or movement of the soil. This portion of the image may then be used to determine a mean optical flow in that region to be set as the offset. This may then be subtracted from the flow to yield the flow in the global frame of reference.

In some embodiments, it may be desirable to identify one or more larger objects within a field of view for tracking movement of soil and/or other material. Accordingly, in such an environment, a clustering algorithm or any other appropriate algorithm may be used to identify objects for tracking movement within a field. The inventors have recognized and appreciated that a number of clustering algorithms may be used for point wise clustering, including density-based spatial clustering of applications with noise (DBSCAN), Affinity Propagation clustering, K-Means clustering, Spectral clustering, and/or any other suitable algorithms.

According to some embodiments, an optical flow may yield a value of velocity in pixels per second for container 130. Additionally, this velocity may be calibrated to yield a dimensional meters per second value for container 130. Subsequently, an average surface soil velocity may be calculated for a region 210 of the image frame corresponding to the location in front of the bucket, as shown in FIG. 2B. The inventors have recognized and appreciated that this may provide the mean soil surface velocity in that region of the image frame. In some embodiments, after the average surface soil velocity is calculated, it may be used to determine the soil's volumetric rate of entry into and/or flow away from the container. The inventors have recognized and appreciated that this may be done using a calibration process. For example, in some embodiments a calibration process may be performed using multiple experimental excavations, with stored measurements of the soil volumetric rate (as explained above) as determined using optical flow measurements and the corresponding final soil volumes in the container. A regression between the total soil flow determined from optical flow and the actual volume of soil may then be determined and used during implementation of the currently disclosed methods. This may allow bucket filling rates determined from optical flow to be scaled to real values.

Figure 3A:
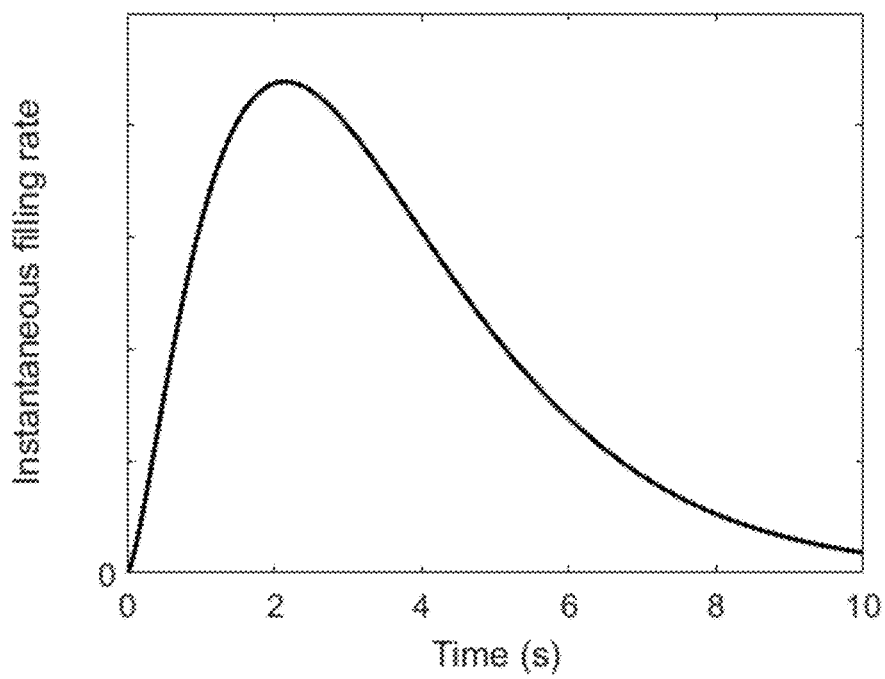
FIG. 3A is an idealized graph of an exemplary normalized filling rate, in accordance with some embodiments.
Figure 3B:
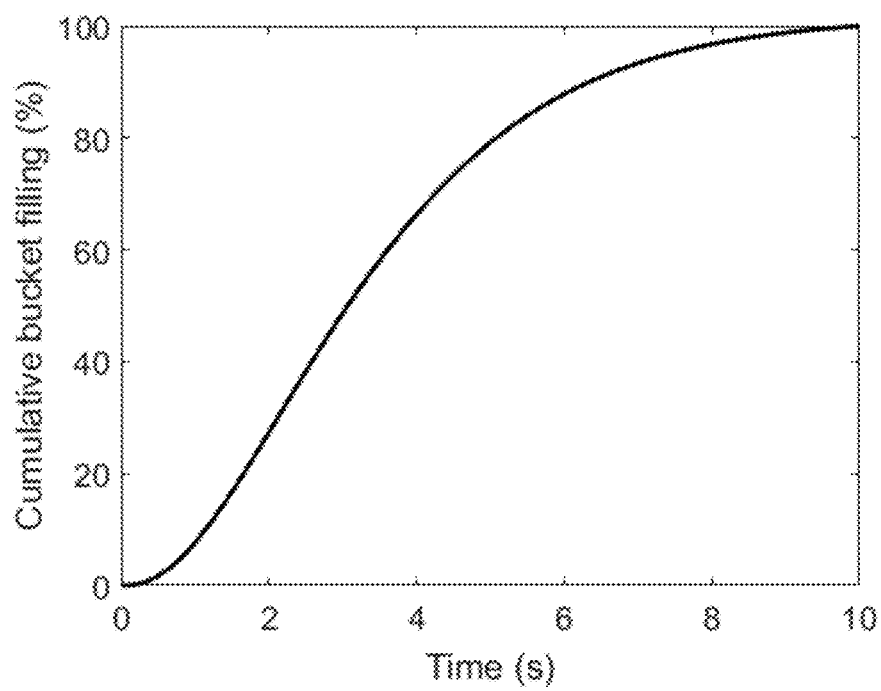
FIG. 3B is an idealized graph of an exemplary normalized cumulative bucket fill, in accordance with some embodiments.

In some embodiments, the total soil in a container may be evaluated as the integration of the instantaneous filling rates during operation. For example, FIG. 3A is an idealized graph of an exemplary normalized filling rate, in accordance with some embodiments; and FIG. 3B is an idealized graph of an exemplary normalized cumulative bucket fill, in accordance with some embodiments. The normalized cumulative bucket fill can be determined from an integration of the normalized filling rate. Alternatively, a slope, inflection point, and/or threshold of the instantaneous filling rate and/or a corresponding magnitude of a flow velocity of soil into the bucket may be correlated with the helpful bucket is. For example, the instantaneous filling rate initially increases to a maximum and then decreases as the bucket becomes progressively more full until eventually the bucket is completely full and any additional soil is simply pushed, i.e. plowed, away from the bucket. Thus, the filling rate and/or flow velocity subsequently decreases and may undergo an inflection point to follow a convex downward sloped curve. Depending on the particular embodiment, an inflection point, a threshold filing rate/flow velocity, and/or a threshold cumulative bucket filling may be used as a control parameter to indicate sufficient filling of the bucket and initiate a desired operation such as terminating digging and scooping the bucket.

In addition to the above, in some embodiments, the inventors have recognized and appreciated that lateral flow of soil relative to a digging direction of a container may be indicative of a filling state of a container. Specifically, lateral flow away from the sides of a container during a digging operation may indicate that the container is full and that the container is not scooping soil into the container and is rather plowing the soil ahead of it. Similar to the above, a threshold magnitude and/or an inflection point in the observed lateral flow of soil may be used to identify a particular fill level of a container.

The inventors have also recognized and appreciated that flow relative to a container may change throughout a digging cycle. Thus, the flow of soil may be evaluated differently during different portions of an excavation cycle. For example, digging at the start of a cycle may be shallower or deeper than during other portions of a cycle depending on the type of system being used. Accordingly, the inventors have recognized and appreciated that the accuracy of determining a fill level of a container may be improved by weighting certain information, such as the time within a cycle, the position and/or orientation of a container relative to the soil, portions of a field of view differently based on empirically determined relationships for that system.

The inventors have recognized and appreciated that visual data can be utilized to identify soil properties directly, and that visual property acquisition has several salient features. For example, visual data acquisition is very quick and easy to capture and analyze, allowing for continuous monitoring of soil properties to provide rapid updates regarding changes in those properties. The continuous update on soil properties can provide input for optimizing digging strategy and trajectory. Furthermore, if visual sensing is implemented, it can provide a sensing system, which is more robust than an equivalent method that uses contact with the soil to measure these properties. The inventors have recognized and appreciated that this is especially true in rugged environments such as mining applications, as contact-free sensing means that very little damage may occur to the work equipment resulting in less maintenance and downtime. Furthermore, the complexity of the system is overwhelmingly on the software side making it easier to improve performance and add functionality with little to no equipment redesign.

The inventors have recognized and appreciated that when one observes the visual data of the container moving through the soil, there is a distinct boundary on the surface of the soil at which point the soil is either moving or stationary. This boundary can be related to the soil failure surface. The soil failure surface is the surface of lowest shear strength within the soil under normal lateral load (as applied by the container). As the bucket applies a force onto the soil, a failure surface extends from the bucket tip until it reaches the soil surface. Under this loading condition, the soil contained within the surface boundary may shear and move relative to the rest of the soil. As the container 130 moves through the soil, the shear boundary may propagate through the soil through successive soil failures resulting in a moving shear surface. In some embodiments, this movement may be captured by an imaging system, as seen where the shear surface meets the top of the soil. By identifying the boundary between moving and stationary soil, one can obtain an estimate of the soil shear layer location.

Figure 9A:
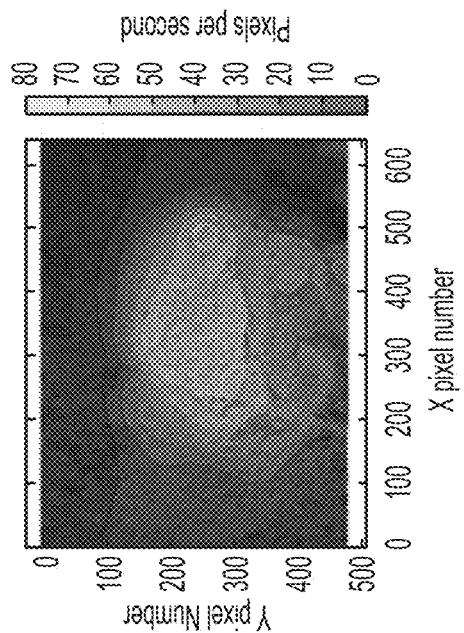
FIGS. 9A-9D are illustrations of exemplary processing of optical flow to obtain a shear layer boundary, in accordance with some embodiments.
Figure 9B:
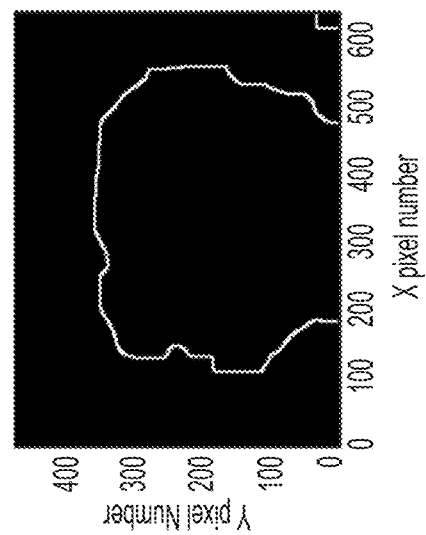
Figure 9C:
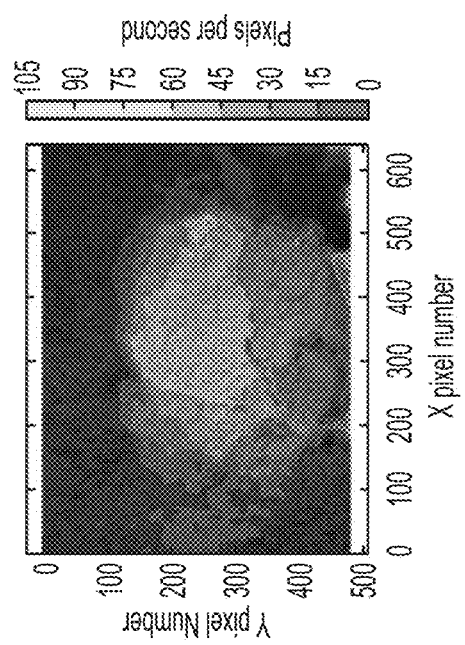
Figure 9D:
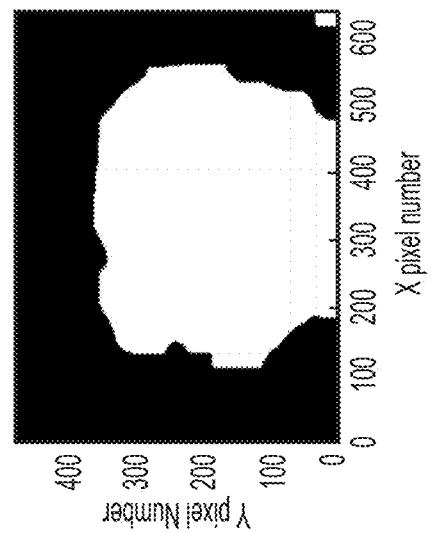

The inventors have recognized and appreciated that a simple method for identifying the shear surface boundary is to set a threshold on the magnitude of velocity and then take the boundary at which the magnitude of the velocity of the soil, or other material, is greater than the threshold velocity to be the boundary. As shown in the example of FIG. 9A, the contours of the velocity form curves of equal velocity. To improve the clarity of the border in the image, after the contours of equal speed have been identified, a 2-dimensional moving average filter may be applied to the velocity values evaluated at each pixel in some embodiments. This may be done through the convolution of the image with a normalized uniform rectangular kernel. The inventors have recognized and appreciated that, as shown in the examples of FIGS. 9A and 9B, the smoothing may improve the ability to distinguish the boundary. After the averaging process, the threshold may be applied and a binary image showing regions above and below the threshold may be obtained. At this point, if the image had small regions that are above the threshold (or below) that are due to noise, a morphological opening may be applied. If a distinct line of the border is desired, the inventors have recognized and appreciated that a Morphological gradient transformation may be applied, an example of which is shown in FIG. 9D.

The inventors have recognized and appreciated that the location of the shear surface may be used to determine certain soil properties. An important soil property for determining digging forces and other soil tool interactions is the soil friction angle. The friction angle is a significant property as it characterizes the shear strength of soil as well as stable slope resting angles that may exist on a soil pile. For this to be evaluated visually, a relation between the location of the shear boundary and the friction may be obtained. The inventors have recognized and appreciated that the simplest way to do this is to use Rankine earth pressure theory, which considers a failure plane extending from the base of the structure feeling the force to the surface of the soil.

The inventors have recognized and appreciated that an important limitation to this method is that it is only possible to distinguish the boundary when the earth and bucket are moving. This leads to erroneous data when the bucket is stationary. To overcome this problem, the measurement of the shear boundary may only be taken when the end effector velocity surpasses a threshold velocity. Despite limitations in relating the observed shear surface location and relating it to the actual true soil characteristics, this estimated version of the friction angle may still be valuable for forming a prediction of forces expected from an arbitrary digging trajectory. If a data driven approach is used, this type of metric, although lacking in a physically accurate interpretation, may still prove useful. Specifically, the digging angle, container trajectory, container velocity, and/or other appropriate operating parameter may be controlled based on the determined shear surface location and/or friction angle.

The above noted soil parameter estimation scheme may be expanded if more information is obtained. For example, the inventors have recognized and appreciated that the use of force measurements at the container and/or at the arm or boom used to apply a digging force to the container may also be used to determine properties of the soil.

The inventors have recognized and appreciated that the grain size of soil has an important bearing on its characteristics. As such, the inventors have recognized and appreciated that it may be useful to obtain this property from visual data. Traditional laboratory methods for determining grain size (sifting or laser diffraction) are limited in their application for use on site due to their slow speed and high expense. On the other hand, visual methods for determining grain size offer a real-time estimate of the grain size in the excavation site using relatively inexpensive equipment. Such visual methods may be separated into two categories: geometric and statistical. Geometric methods use thresholding and other edge detection methods to identify individual grains and calculate their size distribution. This type of method, though, may be limiting when looking at compacted soil (as in this case), as it is difficult to discern an individual grain from its background. On the other hand, statistical methods do not determine individual grain sizes, but rather evaluate a statistical measure of the size distribution. One such method which may be used to analyze textures and characteristic length scales in images is the continuous wavelet transform (CWT). This method is quick and can provide a measure of the distribution of grain size. Traditionally, Wavelets are used to extract spatiotemporal information from a stream of information. In some embodiments, the wavelets can yield local scale information within the image.

Figure 10:
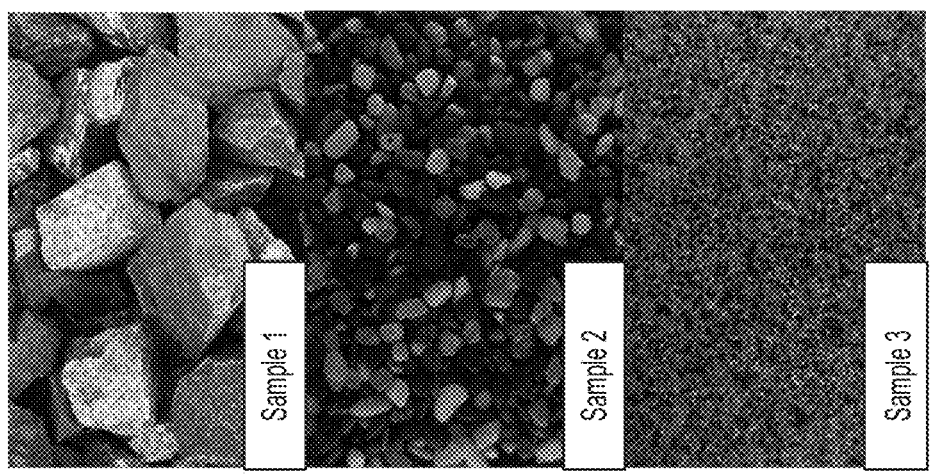
FIG. 10 is a chart and photographs of exemplary non-dimensional size distribution of grain as evaluated in accordance with some embodiments.
Figure 10:
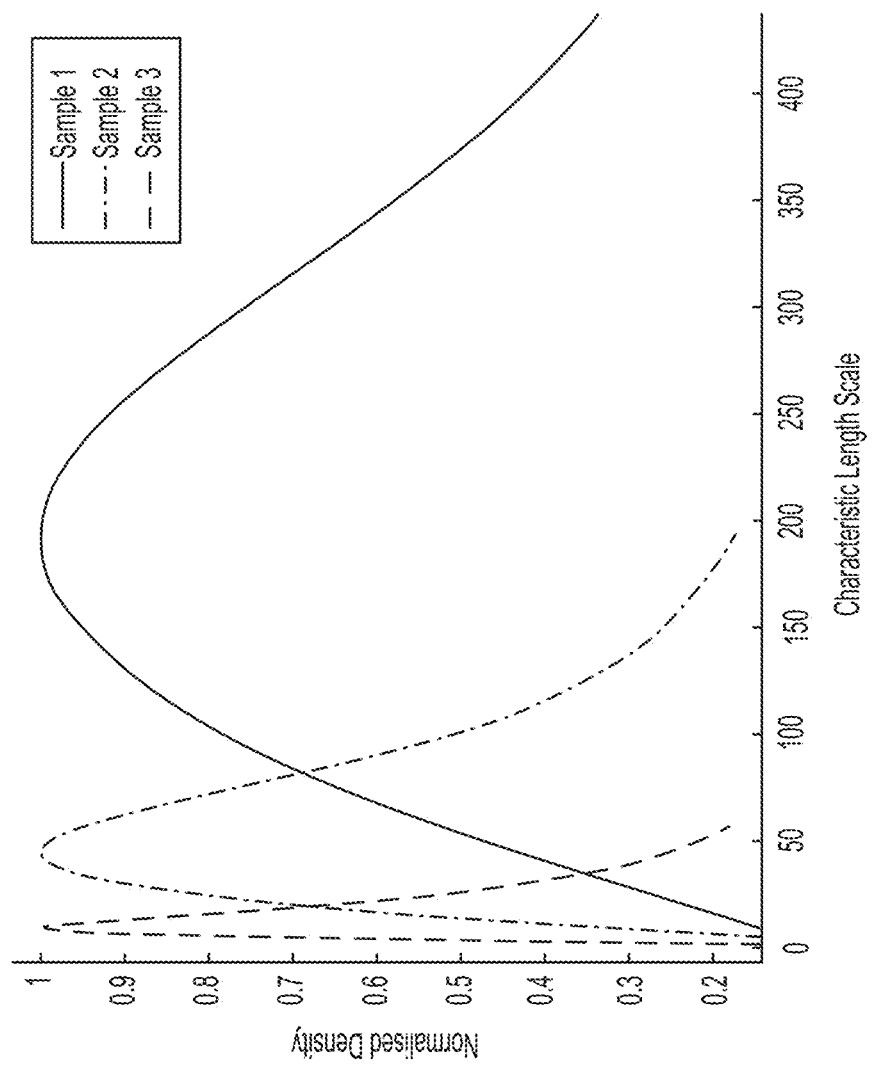

In the above embodiment, CWT may be able to distinguish between rocks of different size, as shown in the examples of FIG. 10 (showing a "Mexican hat" wavelet). The inventors have recognized and appreciated that, with calibration, pixel length scales, and actual dimensions, this may be used to determine the granularity and clumping within soil. An important consideration for this method to work is that the characteristic lengths should be able to be resolved by the image. For large rocks, this may not be a problem, but for finer soils, this may be limited by how close the detector is placed to the soil or the bucket as well as the resolution of the detector.

While specific methods are discussed above, a profile of the soil may also be determined using other methods. For instance, in some embodiments, obtaining a soil profile can be accomplished with a wide range of 3D depth imaging cameras or other detectors. These may provide a measurement of the distance from the detector to the point along the ray corresponding to each pixel. From this data, a 3-dimensional surface corresponding to the soil profile may be determined. The inventors have recognized and appreciated that the 3D image provided by the detector may have a high level of noise, especially when showing the distance to a surface that does not interact favorably with projected IR or other light. To alleviate this effect, the inventors have recognized and appreciated that multiple frames may be captured and the median value between the frames may be used.

The inventors have recognized and appreciated that due to positioning of the camera, lens characteristic of the camera, as well as inherent characteristic of the optics, the raw image from a depth camera or other detector may not directly represent the 3D surface. In some embodiments, two steps of image pre-processing may be applied to correct this distortion: a geometric transformation applied to the image to correct for the distortion of the surface of interest by perspective, and a transformation from the image coordinates to the world coordinates. In some embodiments, this may be done based on a coordinate transformation which compensates for the camera position relative to the ground.

The inventors have recognized and appreciated that the data in its raw form may have many individual pixel values. This may pose a problem when utilizing the data in a predictor since the high dimensionality of the data may prove prohibitively computationally intensive. To deal with this, the inventors have recognized and appreciated that a scheme for compressing the depth data while maintaining meaningfulness may be desired.

The inventors have recognized and appreciated that, due to the relatively smooth nature of the data, a function approximation techniques may be used. Kernel function estimation techniques consist of decomposing an unknown function into a set of simple functions whose combination yields an estimate of the original function. Both global and local variants exist. A global example is the Fourier series decomposition which breaks a function into a series of sines and cosines. Local basis functions are useful for describing a domain with local features. The inventors have recognized and appreciated that the surface of a soil profile may fit this description as it consists of a surface where the important geometric features may be highly isolated from surrounding features. In some embodiments, the method used for this may be the Radial Basis Function (RBF) approximation. Radial Basis Functions are a class of simple real functions which are purely dependent on the norm (here taken as the Euclidean distance) from its origin. This type of function can be used for approximating other curves by adding a group of the radial basis functions together. Given a surface that one wants to estimate (in this case the soil surface), one can arrange grid points at set locations on the (x,y) domain. One may place one radial basis function with its origin on each of the grid points. Then each of these functions may be scaled appropriately based on the value that the surface should take at the location within the grid. For example, an original image including over 210000 pixels may be reduced to a vector of about 200 values.

The inventors have recognized and appreciated that the capture and compression of an earth profile may have several uses, such as parametrization of the earth profile to facilitate control of earth moving equipment, as well as data compression for fast and efficient data transmission.

The inventors have recognized and appreciated that the parametrization of an earth profile may be desirable because it may allow the description of the pertinent geometric parameters of the earth profile, while at the same time rejecting measurement noise. Furthermore, the scaling values may carry a physical interpretation because they represent the amount of soil at a location in the image and thus may carry a more direct bearing on understanding the relation between a trajectory and the change in earth profile.

The inventors have recognized and appreciated that the above noted data compression may also have the added benefit that the transmission of the recorded earth profile to the cloud from excavation sites may be extremely quick, which may assist in several areas. Firstly, this may allow for remote control to work without substantial lag that would otherwise make remote control unfeasible. Furthermore, the quick transmission of the soil profile may allow for rendering of the excavation site at a remote location with relatively low data bandwidth requirements.

According to some embodiments, at least one output may be generated including at least a portion of the captured stream of images overlaid with information relating to the determined state(s) of the soil. For example, a user of the earth moving equipment (either local or remote) may view the output as an interface on a mobile device or other computer, which may provide the user an augmented reality view of the excavation site. In some embodiments, the overlaid information may update in real time with the stream of images, showing at any point details like the bucket filling rate, the bucket fill level, and so on.

Figure 4:
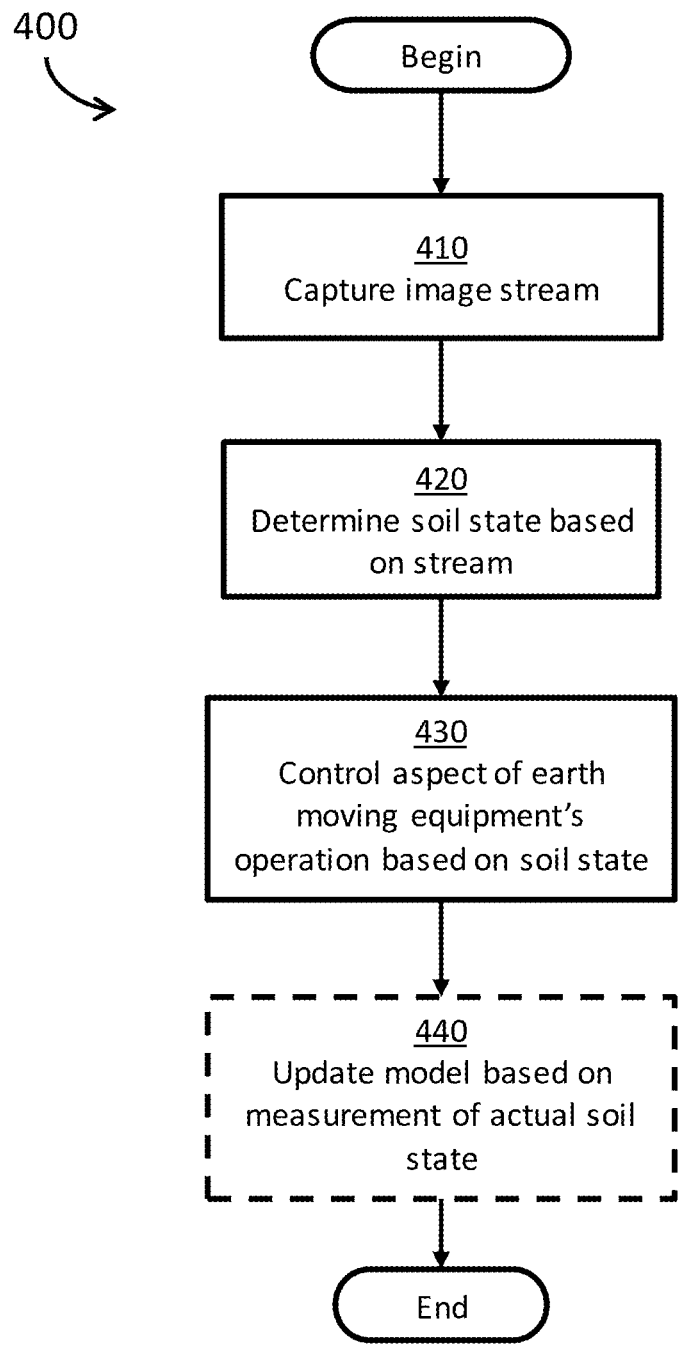
FIG. 4 is a flow chart of an exemplary process that may be implemented in some embodiments.

FIG. 4 is a flow chart of an exemplary process that may be implemented in some embodiments. The process 400 begins at stage 410. At stage 410, a device for controlling earth moving equipment 100 may capture a stream of images from at least one imaging system. The process 400 may then proceed to stage 420. At stage 420, the device may determine at least one state of soil in real time relative to the earth moving equipment based on the captured stream of images as detailed above. The process 400 may then proceed to stage 430. At stage 430, the device may control at least one aspect of the earth moving equipment's operation based on the determined at least one state of the soil, as described above. According to some embodiments, controlling the at least one aspect comprises changing at least one of a trajectory and orientation of a container of the earth moving equipment. In some instances, changing the trajectory and/or orientation of a container may correspond to ending a particular digging cycle, e.g. scooping a container after it has been filled. For example, the operation of the earth moving equipment 100 may correspond to excavating, digging, shoveling, loading, and/or any other suitable operation that may be performed by earth moving equipment like a front shovel, excavator, loader, cable excavator, and/or dragline excavator. The process 400 may then proceed to stage 440. At stage 440, the device may update a model based on a measurement of an actual soil state. For example, a flow-to-volume model may be updated based on a comparison of an estimated or determined fill of the container with a measurement of the actual amount of soil in the container 130. The amount of soil in the container may be determined using a weight of the material within the container measured using any appropriate force parameter (e.g. actuator force, load cell reading, etc.), a depth sensor or other ranging measurement to directly determine filling of the container, and/or any other appropriate method. The process 400 may then end or repeat any suitable number of times.

Figure 5:
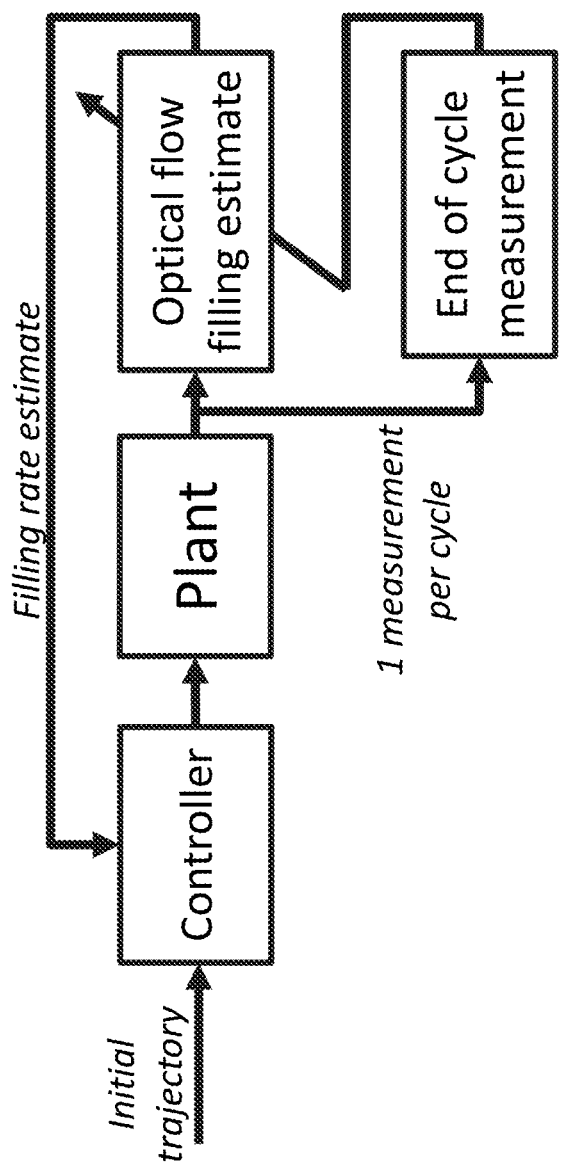
FIG. 5 is a flow chart of an exemplary trajectory adaptation based on a filling estimation, in accordance with some embodiments.

FIG. 5 is a flow chart of an exemplary trajectory adaptation based on a filling estimation of a container, in accordance with some embodiments. As shown in FIG. 5, in some embodiments an initial trajectory is provided to a controller (such as the device discussed herein), which may control the power plant of the earth moving equipment to begin or continue an operation following that trajectory. Then the imaging system may capture image frames as discussed above, and a filling estimate and an end of cycle measurement may be determined. The real time filling estimate may be adapted based on the end of cycle measurement, which may be based on ranging, internal pressure, volume, and/or mass observed in the container. The filling estimate may be returned to the controller to allow learning for future cycles, as discussed in more detail below. The applied trajectories and/or other operating parameters used during a cycle may then be updated for use during future cycles.

Figure 6:
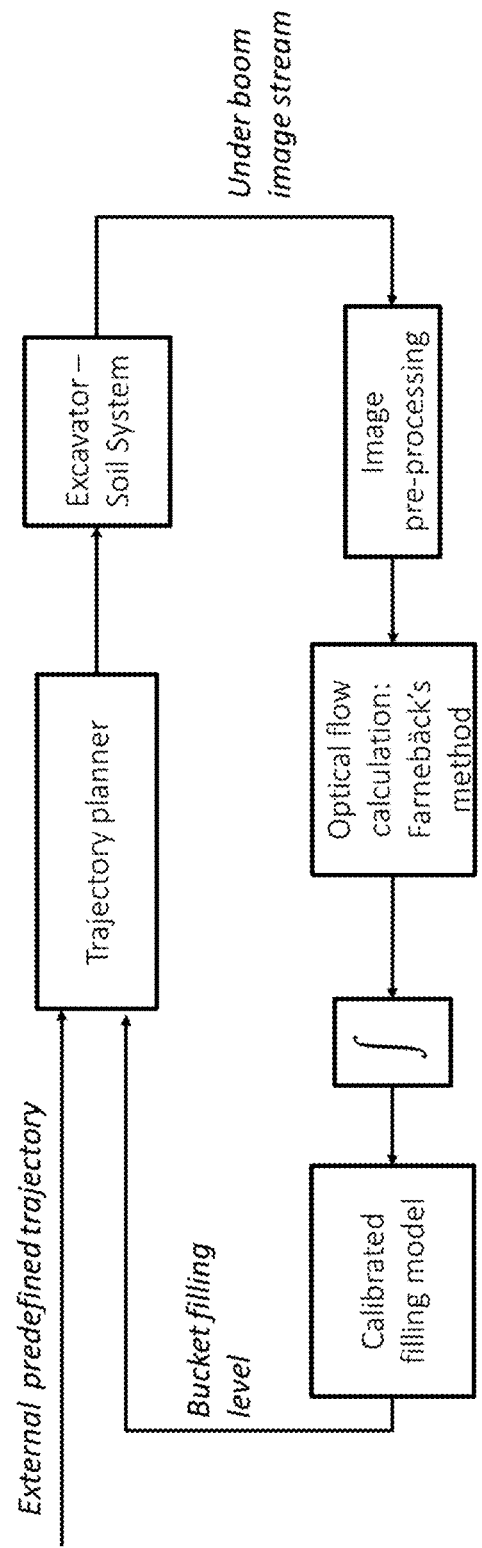
FIG. 6 is a flow chart of an additional exemplary trajectory adaptation based on a filling estimation, in accordance with some embodiments.

FIG. 6 is a flow chart of an additional exemplary trajectory adaptation based on a filling estimation, in accordance with some embodiments. In FIG. 6 a trajectory planner (such as the controller or device described herein) may receive an external predefined trajectory and pass it along to an "excavator-soil system" (such as a piece of earth moving equipment). An imaging system may capture image frames and pre-process those images as described herein. In some embodiments, the Farnebäck method may be used for the optical flow calculation, which may be used to determine the flow rate of soil and the corresponding fill rate of a container. Then integration may be performed as described herein to obtain the fill level of the container, which may be used to update a calibration flow-to-volume model and allow the trajectory planner to adjust the trajectory. However, other methods of determining the fill level of the container as described herein may also be used.

Based on the cumulative fill level of a container, a controller of a system may determine to end a dig trajectory and scoop a container to end a digging cycle. When a threshold value of soil has entered the container, or other metric has been met, the container may be considered full. The trajectory may then be changed to scoop the bucket and terminate the excavation or digging cycle. Alternatively or additionally, the decision to scoop may be based on recognizing a pattern in soil movement using a Convolutional Neural Net. After each digging cycle, the model and/or algorithm used to evaluate the soil state, and/or a filling level of the container, may be further calibrated and/or updated using a corresponding fill level measurement as discussed previously. This updated model and/or algorithm may be used to update future operation of the trajectory planner during subsequent digging cycles.

Figure 7:
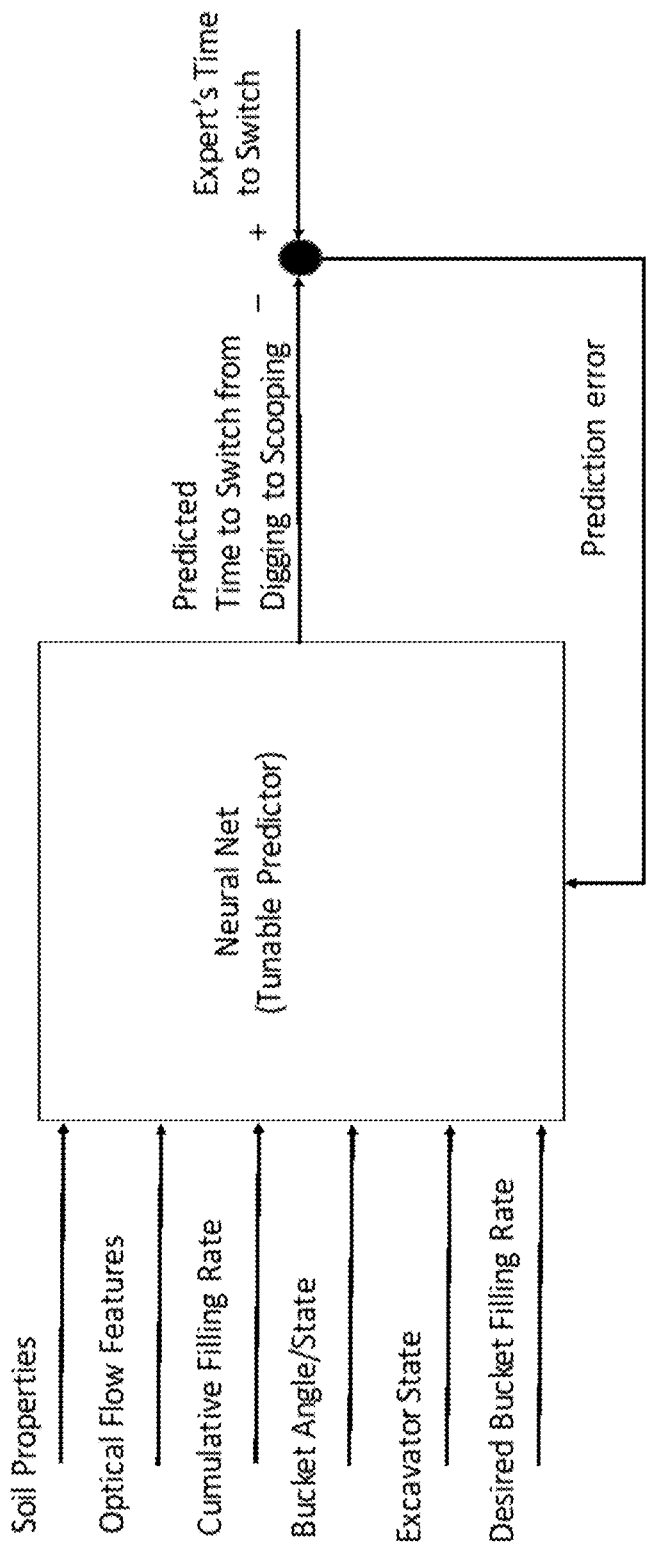
FIG. 7 is a diagram of an exemplary machine learning switching controller, in accordance with some embodiments.

FIG. 7 is a diagram of an exemplary machine learning switching controller, in accordance with some embodiments. According to some embodiments, a large amount of expert demonstration data for one or more operations of a piece of earth moving equipment, including a container operation, may be taken and presented to the tunable/trainable controller/predictor, which may employ a neural network. The discrepancy between the predicted switching timing and the expert switching timing for the desired operation may be fed back to tune the parameters, such as those shown in FIG. 7 and described herein.

The inventors have recognized and appreciated that optimal switching timing can be learned based on human experts' demonstration data. In some embodiments, a trainable controller, such as an Artificial Neural Net, may be used for learning when to switch from digging to scooping operation of an excavator or other piece of earth moving equipment. The input signals to the trainable controller may include, but are not limited to, one or more of a time series filling rate estimation, features of one or more optical flow images (as detected possibly using convolutional neural networks), one or more soil properties (e.g. soil size and other appropriate properties), desired filling rate, one or more states of the container (e.g. bucket angle or other appropriate parameter), and one or more state variables of the excavator or other system. The output from the depicted method may be predicted optimal switching timing which may be compared to that of the timing of a human expert for training the controller. In some instances, a prediction error may be determined by comparing the predicted switching time to the human expert's switching time, and this prediction error may be used for training the controller. Various tuning techniques can be applied, including the standard Error Backpropagation and Convolutional Neural Nets as well as Kernel functions.

Techniques operating according to the principles described herein may be implemented in any suitable manner. Included in the discussion above are flow charts showing the steps and acts of various processes used herein. The processing and decision blocks of the flow chart(s) above represent steps and acts that may be included in algorithms that carry out these various processes. Algorithms derived from these processes may be implemented as software integrated with and directing the operation of one or more single- or multi-purpose processors, may be implemented as functionally-equivalent circuits such as a Digital Signal Processing (DSP) circuit or an Application-Specific Integrated Circuit (ASIC), or may be implemented in any other suitable manner. It should be appreciated that the flow chart(s) included herein do not depict the syntax or operation of any particular circuit or of any particular programming language or type of programming language. Rather, the flow chart(s) illustrate the functional information one skilled in the art may use to fabricate circuits or to implement computer software algorithms to perform the processing of a particular apparatus carrying out the types of techniques described herein. It should also be appreciated that, unless otherwise indicated herein, the particular sequence of steps and/or acts described in each flow chart is merely illustrative of the algorithms that may be implemented and can be varied in implementations and embodiments of the principles described herein.

Accordingly, in some embodiments, the techniques described herein may be embodied in computer-executable instructions implemented as software, including as application software, system software, firmware, middleware, embedded code, or any other suitable type of computer code. Such computer-executable instructions may be written using any of a number of suitable programming languages and/or programming or scripting tools, and also may be compiled as executable machine language code or intermediate code that is executed on a framework or virtual machine.

When techniques described herein are embodied as computer-executable instructions, these computer-executable instructions may be implemented in any suitable manner, including as a number of functional facilities, each providing one or more operations to complete execution of algorithms operating according to these techniques. A "functional facility," however instantiated, is a structural component of a computer system that, when integrated with and executed by one or more computers, causes the one or more computers to perform a specific operational role. A functional facility may be a portion of or an entire software element. For example, a functional facility may be implemented as a function of a process, or as a discrete process, or as any other suitable unit of processing. If techniques described herein are implemented as multiple functional facilities, each functional facility may be implemented in its own way, all need not be implemented the same way. Additionally, these functional facilities may be executed in parallel and/or serially, as appropriate, and may pass information between one another using a shared memory on the computer(s) on which they are executing, using a message passing protocol, or in any other suitable way.

Generally, functional facilities include routines, programs, objects, components, data structures, etc. that perform particular tasks or implement particular abstract data types. Typically, the functionality of the functional facilities may be combined or distributed as desired in the systems in which they operate. In some implementations, one or more functional facilities carrying out techniques herein may together form a complete software package. These functional facilities may, in alternative embodiments, be adapted to interact with other, unrelated functional facilities and/or processes, to implement a software program application.

Some exemplary functional facilities have been described herein for carrying out one or more tasks. It should be appreciated, though, that the functional facilities and division of tasks described is merely illustrative of the type of functional facilities that may implement the exemplary techniques described herein, and that embodiments are not limited to being implemented in any specific number, division, or type of functional facilities. In some implementations, all functionality may be implemented in a single functional facility. It should also be appreciated that, in some implementations, some of the functional facilities described herein may be implemented together with or separately from others (i.e., as a single unit or separate units), or some of these functional facilities may not be implemented.

In some, but not all, implementations in which the techniques may be embodied as computer-executable instructions, these instructions may be executed on one or more suitable computing device(s) operating in any suitable computer system, or one or more computing devices (or one or more processors of one or more computing devices) may be programmed to execute the computer-executable instructions. A computing device or processor may be programmed to execute instructions when the instructions are stored in a manner accessible to the computing device or processor, such as in a data store (e.g., an on-chip cache or instruction register, a computer-readable storage medium accessible via a bus, a computer-readable storage medium accessible via one or more networks and accessible by the device/processor, etc.). Functional facilities comprising these computer-executable instructions may be integrated with and direct the operation of a single multi-purpose programmable digital computing device, a coordinated system of two or more multi-purpose computing device sharing processing power and jointly carrying out the techniques described herein, a single computing device or coordinated system of computing device (co-located or geographically distributed) dedicated to executing the techniques described herein, one or more Field-Programmable Gate Arrays (FPGAs) for carrying out the techniques described herein, or any other suitable system.

Figure 8:
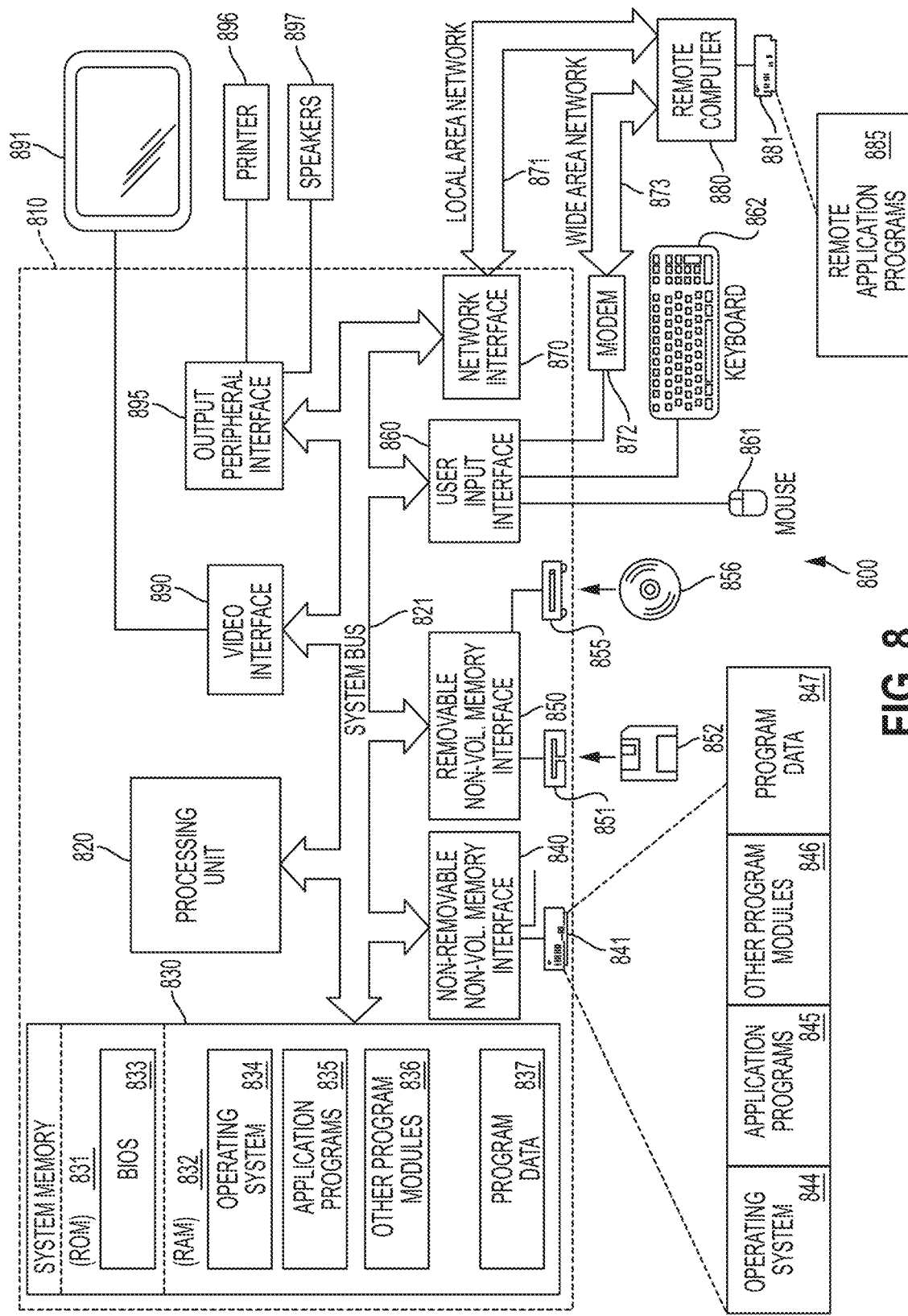
FIG. 8 is a block diagram of a computing device with which some embodiments may operate.

FIG. 8 illustrates an example of a suitable computing system environment 800 on which some embodiments may operate. The computing system environment 800 is only one example of a suitable computing environment and is not intended to suggest any limitation as to the scope of use or functionality of the application. Neither should the computing environment 800 be interpreted as having any dependency or requirement relating to any one or combination of components illustrated in the exemplary operating environment 800.

Some embodiments of the application are operational with numerous special purpose or multi-purpose computing system environments or configurations. Examples of well-known computing systems, environments, and/or configurations that may be suitable include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or to devices, and the like.

The computing environment may execute computer-executable instructions, such as program modules. Generally, program modules include routines, programs, objects, components, data structures, etc. that perform particular tasks or implement particular abstract data types. The application may also be practiced in distributed computing environments where tasks are performed by remote processing devices that are linked through a communications network. In a distributed computing environment, program modules may be located in both local and remote computer storage media including memory storage devices.

With reference to FIG. 8, an exemplary system for implementing some embodiments of the application includes a computing device in the form of a computer 810. Computer 810, with programming or other modification to perform functions as described herein may be used to implement a device for controlling earth moving equipment. Alternatively or additionally, device 810, rather than being dedicated to a particular task, may be a computer that would, in normal operation, store or retrieve information from a storage device.

Components of computer 810 may include, but are not limited to, a processing unit 820, a system memory 830, and a system bus 821 that couples various system components including the system memory to the processing unit 820. The system bus 821 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 810 typically includes a variety of computer readable media. Computer readable media can be any available media that can be accessed by computer 810 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules, or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 810. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared, and other wireless media. Combinations of the any of the above should also be included within the scope of computer readable media.

The system memory 830 includes computer storage media in the form of volatile and/or nonvolatile memory such as read only memory (ROM) 831 and random access memory (RAM) 832. A basic input/output system 833 (BIOS), containing the basic routines that help to transfer information between elements within computer 810, such as during start-up, is typically stored in ROM 831. RAM 832 typically contains data and/or program modules that are immediately accessible to and/or presently being operated on by processing unit 820. By way of example, and not limitation, FIG. 8 illustrates operating system 834, application programs 835, other program modules 836, and program data 837.

The computer 810 may also include other removable/non-removable, volatile/nonvolatile computer storage media. By way of example only, FIG. 8 illustrates a hard disk drive 841 that reads from or writes to non-removable, nonvolatile magnetic media, a magnetic disk drive 851 that reads from or writes to a removable, nonvolatile magnetic disk 852, and an optical disk drive 855 that reads from or writes to a removable, nonvolatile optical disk 856 such as a CD-ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 841 is typically connected to the system bus 821 through a non-removable memory interface such as interface 840, and magnetic disk drive 851 and optical disk drive 855 are typically connected to the system bus 821 by a removable memory interface, such as interface 850.

The drives and their associated computer storage media discussed above and illustrated in FIG. 8, provide storage of computer readable instructions, data structures, program modules and other data for the computer 810. In FIG. 8, for example, hard disk drive 841 is illustrated as storing operating system 844, application programs 845, other program modules 846, and program data 847. Note that these components can either be the same as or different from operating system 834, application programs 835, other program modules 836, and program data 837. Operating system 844, application programs 845, other program modules 846, and program data 847 are given different numbers here to illustrate that, at a minimum, they are different copies. A user may enter commands and information into the computer 810 through input devices such as a keyboard 862 and pointing device 861, commonly referred to as a mouse, trackball, or touch pad. Other input devices (not shown) may include a microphone, joystick, game pad, satellite dish, scanner, or the like. These and other input devices are often connected to the processing unit 820 through a user input interface 860 that is coupled to the system bus, but may be connected by other interface and bus structures, such as a parallel port, game port or a universal serial bus (USB). A monitor 891 or other type of display device is also connected to the system bus 821 via an interface, such as a video interface 890. In addition to the monitor, computers may also include other peripheral output devices such as speakers 897 and printer 896, which may be connected through a output peripheral interface 895.

The computer 810 may operate in a networked environment using logical connections to one or more remote computers, such as a remote computer 880. The remote computer 880 may be a personal computer, a server, a router, a network PC, a peer device, or other common network node, and typically includes many or all of the elements described above relative to the computer 810, although only a memory storage device 881 has been illustrated in FIG. 8. The logical connections depicted in FIG. 8 include a local area network (LAN) 871 and a wide area network (WAN) 873, but may also include other networks. Such networking environments are commonplace in offices, enterprise-wide computer networks, intranets, and the Internet.

When used in a LAN networking environment, the computer 810 is connected to the LAN 871 through a network interface or adapter 870. When used in a WAN networking environment, the computer 810 typically includes a modem 872 or other means for establishing communications over the WAN 873, such as the Internet. The modem 872, which may be internal or external, may be connected to the system bus 821 via the user input interface 860, or other appropriate mechanism. In a networked environment, program modules depicted relative to the computer 810, or portions thereof may be stored in the remote memory storage device. By way of example, and not limitation, FIG. 8 illustrates remote application programs 885 as residing on memory device 881. It will be appreciated that the network connections shown are exemplary and other means of establishing a communications link between the computers may be used.

Having thus described several aspects of at least one embodiment of this application, it is to be appreciated that various alterations, modifications, and improvements will readily occur to those skilled in the art.

Such alterations, modifications, and improvements are intended to be part of this disclosure, and are intended to be within the spirit and scope of the application. Further, though advantages of the present application are indicated, it should be appreciated that not every embodiment will include every described advantage. Some embodiments may not implement any features described as advantageous herein and in some instances. Accordingly, the foregoing description and drawings are by way of example only.

The above-described embodiments can be implemented in any of numerous ways. For example, the embodiments may be implemented using hardware, software, or a combination thereof. When implemented in software, the software code can be executed on any suitable processor or collection of processors, whether provided in a single computer or distributed among multiple computers. Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semicustom circuitry resulting from configuring a programmable logic device. As yet a further alternative, a processor may be a portion of a larger circuit or semiconductor device, whether commercially available, semi-custom, or custom. As a specific example, some commercially available microprocessors have multiple cores such that one or a subset of those cores may constitute a processor. Though, a processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone, or any other suitable portable or fixed electronic device.

Also, a computer may have one or more input and output devices. These devices can be used, among other things, to present a user interface. Examples of output devices that can be used to provide a user interface include painters or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks, or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the application may be embodied as a computer readable storage medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the application discussed above. As is apparent from the foregoing examples, a computer readable storage medium may retain information for a sufficient time to provide computer-executable instructions in a non-transitory form.

Tangible storage media have at least one physical, structural component. In a "computer-readable medium," as used herein, at least one physical, structural component has at least one physical property that may be altered in some way during a process of creating the medium with embedded information, a process of recording information thereon, or any other process of encoding the medium with information. For example, a magnetization state of a portion of a physical structure of a computer-readable medium may be altered during a recording process.

Such a computer readable storage medium or media can be transportable, such that the program or programs stored thereon can be loaded onto one or more different computers or other processors to implement various aspects of the present application as discussed above. As used herein, the term "computer-readable storage medium" encompasses only a computer-readable medium that can be considered to be a manufacture (i.e., article of manufacture) or a machine. Alternatively or additionally, the application may be embodied as a computer readable medium other than a computer-readable storage medium, such as a propagating signal.

The terms "program" or "software" are used herein in a generic sense to refer to any type of computer code or set of computer-executable instructions that can be employed to program a computer or other processor to implement various aspects of the present application as discussed above. Additionally, it should be appreciated that according to one aspect of this embodiment, one or more computer programs that when executed perform methods of the present application need not reside on a single computer or processor, but may be distributed in a modular fashion amongst a number of different computers or processors to implement various aspects of the present application.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags, or other mechanisms that establish relationship between data elements.

Embodiments have been described where the techniques are implemented in circuitry and/or computer-executable instructions. It should be appreciated that some embodiments may be in the form of a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Having thus described several aspects of at least one embodiment of this application, it is to be appreciated that various alterations, modifications, and improvements will readily occur to those skilled in the art.

Such alterations, modifications, and improvements are intended to be part of this disclosure, and are intended to be within the spirit and scope of the application. Further, though advantages of the present application are indicated, it should be appreciated that not every embodiment will include every described advantage. Some embodiments may not implement any features described as advantageous herein and in some instances. Accordingly, the foregoing description and drawings are by way of example only.

Various aspects of the embodiments described above may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items.

The word "exemplary" is used herein to mean serving as an example, instance, or illustration. Any embodiment, implementation, process, feature, etc. described herein as exemplary should therefore be understood to be an illustrative example and should not be understood to be a preferred or advantageous example unless otherwise indicated.

Having thus described several aspects of at least one embodiment, it is to be appreciated that various alterations, modifications, and improvements will readily occur to those skilled in the art. Such alterations, modifications, and improvements are intended to be part of this disclosure, and are intended to be within the spirit and scope of the principles described herein. Accordingly, the foregoing description and drawings are by way of example only.

What is claimed is:

1. A piece of earth moving equipment, the earth moving equipment comprising:
   at least one container; and
   at least one processor configured to:
   determine at least one state of soil, including at least one flow rate of the soil relative to the at least one container of the earth moving equipment, in real time relative to the earth moving equipment based on a captured stream of images at least by evaluating differential motion between two or more image frames of the captured stream of images,
   wherein evaluating the differential motion comprises identifying one or more features within the two or more image frames and determining a relative motion of at least one of the one or more features; and
   control, without need of a human operator, at least one aspect of the earth moving equipment's operation based on the determined at least one state of the soil at least by selecting between digging and scooping of the soil with the at least one container of the earth moving equipment based on recognizing a pattern in soil movement using at least one neural network.

2. The earth moving equipment of claim 1, further comprising at least one imaging system, and wherein the at least one processor is configured to capture the stream of images from the at least one imaging system.

3. The earth moving equipment of claim 2, wherein the at least one processor is configured to:
   determine the at least one state of the soil at least by determining a total amount of soil in the at least one container of the earth moving equipment based on the at least one flow rate; and
   determine a fill rate of the at least one container of the earth moving equipment based on the at least one flow rate.

4. The earth moving equipment of claim 1, wherein the at least one state of the soil comprises at least one property of the soil including at least one of a shear failure surface of the soil, a friction angle of the soil, and a granularity of the soil.

5. The earth moving equipment of claim 1, wherein the at least one processor is configured to:
   detect areas of soil movement within a field of view; and
   determine the at least one state of the soil based on the detected areas of soil movement within the field of view.

6. The earth moving equipment of claim 1, wherein the at least one processor is further configured to:
   detect soil movement in front of a leading edge of the at least one container of the earth moving equipment; and
   determine the at least one state of the soil based on the detected soil movement in front of the leading edge of the at least one container of the earth moving equipment.

7. The earth moving equipment of claim 1, wherein the at least one processor is further configured to update a flow-to-volume model via learning based on a measurement of an actual total amount of soil in the at least one container of the earth moving equipment.

8. A method for controlling earth moving equipment, the method comprising:
   determining at least one state of soil, including at least one flow rate of the soil relative to at least one container of the earth moving equipment, in real time relative to the earth moving equipment based on a captured stream of images at least by evaluating differential motion between two or more image frames of the captured stream of images, wherein evaluating the differential motion comprises identifying one or more features within the two or more image frames and determining a relative motion of at least one of the one or more features; and
   controlling, without need of a human operator, at least one aspect of the earth moving equipment's operation based on the determined at least one state of the soil, at least by selecting between digging and scooping of the soil with the at least one container of the earth moving equipment based on recognizing a pattern in soil movement using at least one neural network.

9. The method of claim 8, further comprising capturing the stream of images from at least one imaging system.

10. The method of claim 8, further comprising:
    detecting areas of soil movement within a field of view; and
    determining the at least one state of the soil based on the detected areas of soil movement within the field of view.

11. The method of claim 8, further comprising updating a flow-to-volume model via learning based on a measurement of an actual total amount of soil in the at least one container of the earth moving equipment.

12. At least one non-transitory computer-readable medium having instructions thereon that, when executed by at least one processor, perform a method for controlling earth moving equipment, the method comprising:
    determining at least one state of soil, including at least one flow rate of the soil relative to at least one container of the earth moving equipment, in real time relative to the earth moving equipment based on a captured stream of images at least by evaluating differential motion between two or more image frames of the captured stream of images, wherein evaluating the differential motion comprises identifying one or more features within the two or more image frames and determining a relative motion of at least one of the one or more features; and controlling, without need of a human operator, at least one aspect of the earth moving equipment's operation based on the determined at least one state of the soil, at least by selecting between digging and scooping of the soil with the at least one container of the earth moving equipment based on recognizing a pattern in soil movement using at least one neural network.

13. The at least one non-transitory computer-readable medium of claim 12, the method further comprising capturing a stream of images from at least one imaging system.

14. The at least one non-transitory computer-readable medium of claim 12, wherein determining the at least one state of the soil comprises determining a total amount of soil in the at least one container of the earth moving equipment based on at least one flow rate, and the method comprises determining a fill rate of the at least one container of the earth moving equipment based on the at least one flow rate.

15. The at least one non-transitory computer-readable medium of claim 12, the method further comprising:
  detecting areas of soil movement within a field of view; and
  determining the at least one state of the soil based on the detected areas of soil movement within the field of view.

16. The at least one non-transitory computer-readable medium of claim 12, the method further comprising:
  detecting soil movement in front of a leading edge of the at least one container of the earth moving equipment; and
  determining the at least one state of the soil based on the detected soil movement in front of the leading edge of the at least one container of the earth moving equipment.

17. The at least one non-transitory computer-readable medium of claim 12, the method further comprising updating a flow-to-volume model via learning based on a measurement of an actual total amount of soil in the at least one container of the earth moving equipment.

18. The earth moving equipment of claim 1, wherein evaluating the differential motion comprises applying phase correlation, a two-dimensional median filter, and/or flow adapted anisotropic diffusion.

19. The method of claim 8, wherein evaluating the differential motion comprises applying phase correlation, a two-dimensional median filter, and/or flow adapted anisotropic diffusion.

20. The at least one non-transitory computer-readable medium of claim 12, wherein evaluating the differential motion comprises applying phase correlation, a two-dimensional median filter, and/or flow adapted anisotropic diffusion.

21. The earth moving equipment of claim 1, wherein the at least one processor is configured to control the at least one aspect of the earth moving equipment's operation at least by changing at least one of a trajectory and orientation of the at least one container of the earth moving equipment.

22. The method of claim 8, wherein controlling the at least one aspect of the earth moving equipment's operation comprises changing at least one of a trajectory and orientation of the at least one container of the earth moving equipment.

23. The at least one non-transitory computer-readable medium of claim 12, wherein controlling the at least one aspect of the earth moving equipment's operation comprises changing at least one of a trajectory and orientation of the at least one container of the earth moving equipment.

* * * * *